United States Patent
Ishizuka

(10) Patent No.: US 6,585,640 B2
(45) Date of Patent: Jul. 1, 2003

(54) METHOD FOR CONTROLLING RELATIVE DEFORMATION BETWEEN AN ENDOSCOPE AND COMPONENTS THEREOF

(75) Inventor: Tatsuya Ishizuka, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 21 days.

(21) Appl. No.: 09/887,819

(22) Filed: Jun. 22, 2001

(65) Prior Publication Data

US 2002/0002322 A1 Jan. 3, 2002

(30) Foreign Application Priority Data

Jun. 23, 2000 (JP) ....................................... 2000-189919

(51) Int. Cl.⁷ ............................................... A61B 1/00
(52) U.S. Cl. ....................... 600/133; 600/139; 600/920
(58) Field of Search ............................... 600/139, 133, 600/140, 143, 151, 130, 920

(56) References Cited

U.S. PATENT DOCUMENTS

| | | | | |
|---|---|---|---|---|
| 5,394,864 A | * | 3/1995 | Kobayashi et al. | 600/133 |
| 5,443,057 A | * | 8/1995 | Elmore | 600/133 |
| 6,146,326 A | * | 11/2000 | Pollack et al. | 600/133 |
| 6,419,628 B1 | * | 7/2002 | Rudischhauser et al. | 600/130 |

FOREIGN PATENT DOCUMENTS

JP 10-276968 10/1998

* cited by examiner

Primary Examiner—Linda C. M. Dvorak
Assistant Examiner—Jocelyn Ram
(74) Attorney, Agent, or Firm—Scully, Scott, Murphy & Presser

(57) ABSTRACT

An endoscope where problems due to a difference of deformation amount in the longitudinal direction generated between the flexible tube and the integrated object during autoclave sterilization are prevented, wherein the insertion part is comprised of a hard tip part and a flexible tube which is linked to the base of the hard tip part via a curving part, the tip of a treatment instrument tube is secured to a metal pipe disposed in a through hole of the hard tip part, the base part is secured to a branch pipe, and the treatment instrument tube has a shrinkage factor x having a characteristic x<1, that is, shrinking after a predetermined thermal load is applied, whereas the flexible tube 15 has shrinkage a factor y having a characteristic y<1, that is, shrinking after a predetermined thermal load is applied, in other words, the deforming directions of the flexible tube and the treatment instrument tube are set to the same direction with respect to the longitudinal direction, so that the flexible tube and the treatment instrument tube shrink in the same direction when the endoscope is exposed to such a thermal load environment as autoclave sterilization.

13 Claims, 6 Drawing Sheets

METHOD FOR CONTROLLING RELATIVE DEFORMATION BETWEEN AN ENDOSCOPE AND COMPONENTS THEREOF

This application claims benefit of Japanese Application No. 2000-189919 filed in Japan on Jun. 23, 2000, the contents of which are incorporated by this reference.

BACKGROUND OF THE INVENTION

1. Field of the Invention

The present invention relates to an endoscope, and more particularly to an endoscope having a soft flexible tube in the insertion part wherein at least one elongated integrated object is disposed in the flexible tube.

2. Description of the Related Art

An endoscope for medicine which is inserted into the body for observing internal organs by inserting the elongated insertion part, or allows various treatments using a treatment instrument inserted into the treatment instrument channel if required is widely used.

Particularly an endoscope used in the medical field is used for observing internal organs by inserting the insertion part into the body or allows medical treatment using a treatment instrument inserted in the treatment instrument channel of the endoscope. Therefore cleaning and disinfecting the endoscope device must be performed after inspection and treatment end when an endoscope and treatment instruments used once are used again for another patient, so that infection between patients via the endoscope and instruments is prevented.

Recently autoclave sterilization, which does not involve a complicated operation, and which allows using the equipment immediately after sterilization with low running cost, is becoming the standard sterilization processing of a medical instrument.

Japanese Unexamined patent publication No. H10-276968 discloses an endoscope wherein a fluororesin tube is used for the flexible tube enclosed to pass fluid or treatment instruments, and annealing is performed before incorporating the fluororesin tube into the endoscope, so that the internal tube does not shrink when sterilization is performed by autoclaving, and sufficient sterilization processing can be performed repeatedly.

However, in the case of the endoscope in Japanese Unexamined patent publication No. H10-276968, annealing processing on the fluororesin tube is performed before incorporating the tube into the endoscope, so if the endoscope is autoclaved, for example, the flexible tube constituting the insertion part which is not annealed may shrink in the longitudinal direction by thermal load during autoclaving.

In other words, the entire flexible tube shrinks, and the annealed fluororesin tube inside the flexible tube hardly shrinks. Therefore the fluororesin tube becomes loose compared with the flexible tube, and the tube itself may be easily buckled.

Also other objects integrated inside the flexible tube, such as a light guide for supplying illuminating light (hereinafter "light guide") and a signal transmission cable for transmitting electric signals from an image pick-up means, are pressed by a loosened tube, and the movement of these objects is obstructed or such problems as the buckling of integrated objects and cable disconnection occur.

Also, when annealing the fluororesin tube incorporated into the endoscope, normally several loops of long fluororesin tube are placed in a furnace for annealing. This curls the fluororesin tube, which makes it difficult to incorporate the tube into the endoscope. If a curled fluororesin tube is incorporated into the endoscope, this fluororesin tube obstructs the movement of the integrated objects, such as a light guide and signal transmission cable, which are pressed by the fluororesin tube, and such problems as buckling and disconnection may occur, also the curl of the tube may negatively affect the insertion of the endoscope itself.

Incorporating an unannealed fluororesin tube into the endoscope has been widely performed. However, if this endoscope is autoclaved, the unannealed fluororesin tube shrinks in the longitudinal direction. Then the fluororesin tube is pulled from both ends of the flexible tube, load is applied to the connection parts at both ends of the fluororesin tube, and problems may occur.

SUMMARY OF THE INVENTION

With the foregoing in view, it is an object of the present invention to provide an endoscope where problems due to an increase in the difference of the deformation amount in the longitudinal direction between the flexible tube and an integrated object during autoclaving are prevented.

An endoscope according to the present invention is an endoscope which comprises a flexible insertion part having an elongated flexible tube, and at least one elongated integrated object which is directly or indirectly secured to both ends of said flexible tube, wherein there is disposed deformation control means for controlling an increase of the absolute value of the difference between the deformation amounts in the longitudinal direction of said flexible tube and said at least one elongated integrated object with respect to a predetermined thermal load.

Also, according to the present invention, the endoscope which comprises an insert part having an elongated flexible tube, and at least one elongated integrated object which is directly or indirectly secured to both ends of said flexible tube, wherein the shrinkage factors of said flexible tube and said integrated object in the longitudinal direction with respect to a predetermined thermal load are roughly the same.

Further, according to the present invention, the endoscope comprising an insertion part having an elongated flexible tube, and at least one elongated integrated object which is directly or indirectly secured to both ends of said flexible tube, wherein the deformation amount in the longitudinal direction and deforming directions of said flexible tube and said integrated object with respect to a predetermined thermal load are roughly the same.

The above and other objects, features and advantages of the invention will become more apparent from the following description when taken in conjunction with the accompanying drawings.

BRIEF DESCRIPTION OF THE DRAWINGS

FIGS. 1 to FIG. 4 are related to an embodiment of the present invention, and FIG. 1 is a diagram depicting a general configuration of the endoscope device;

FIG. 2 is a diagram depicting an example of a configuration of the insertion part;

DESCRIPTION OF THE PREFERRED EMBODIMENTS

Embodiments of the present invention will now be described with reference to the accompanying drawings.

Figure 1:
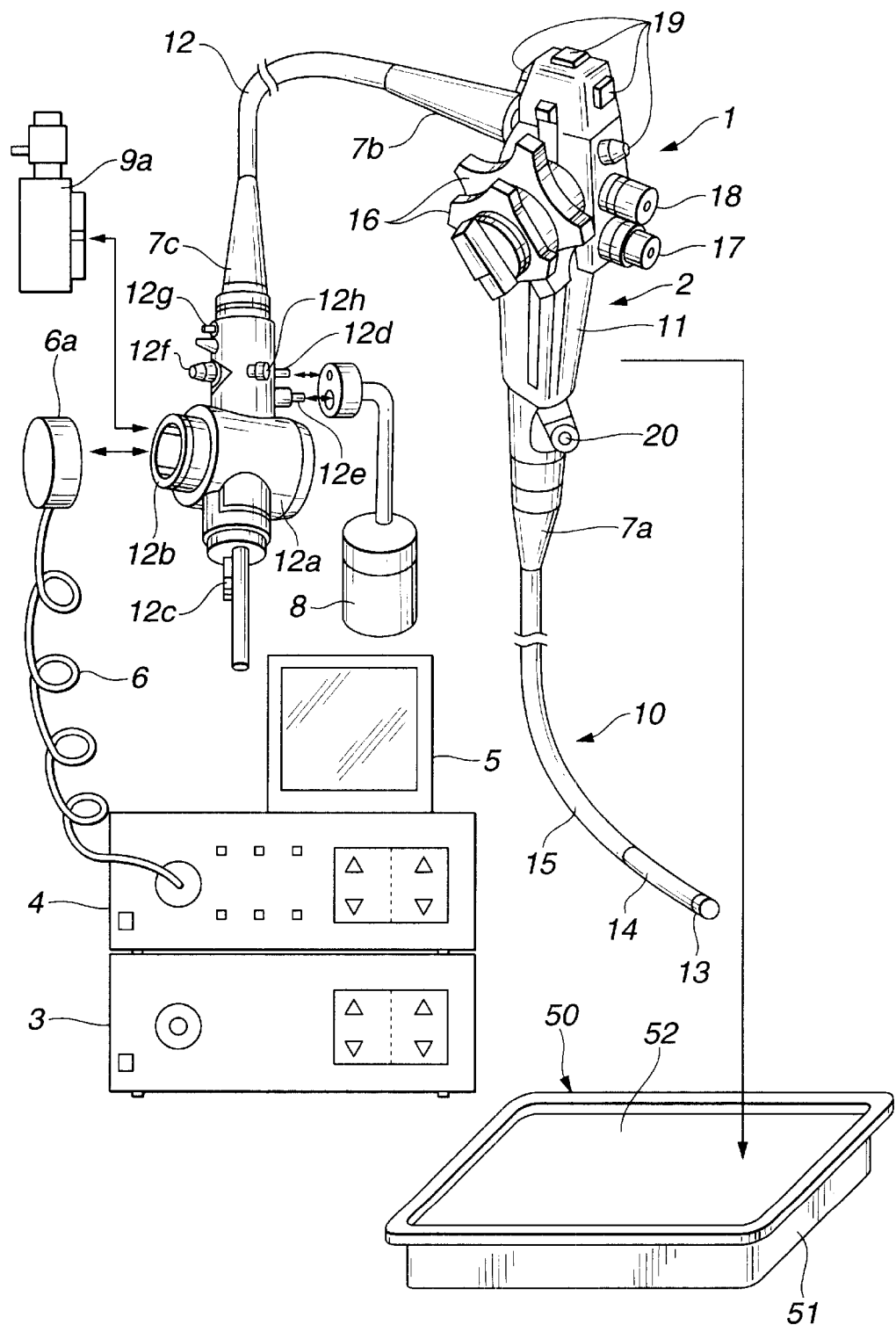
Figure 2:
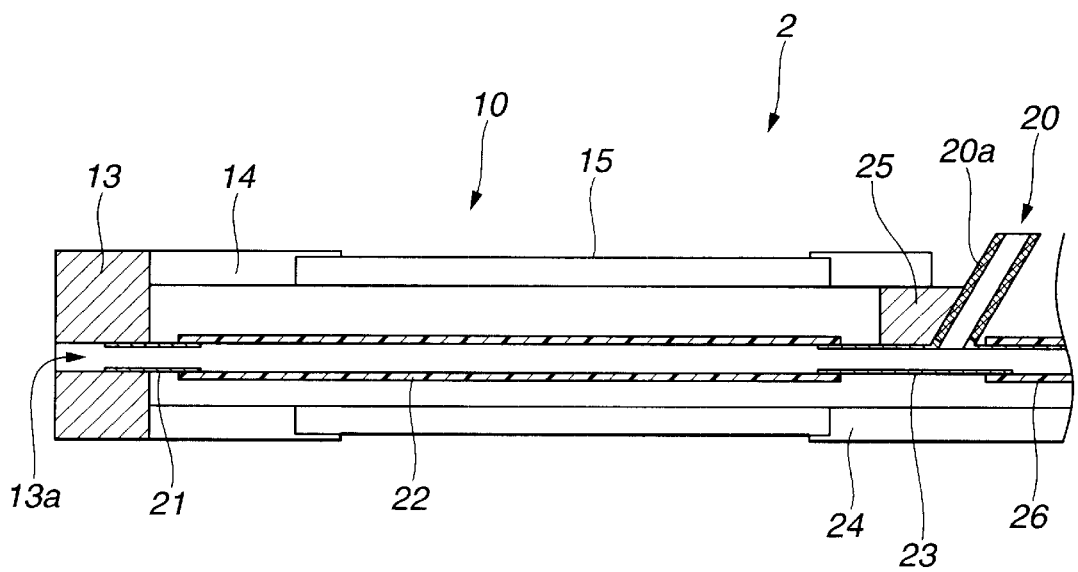
Figure 3A:
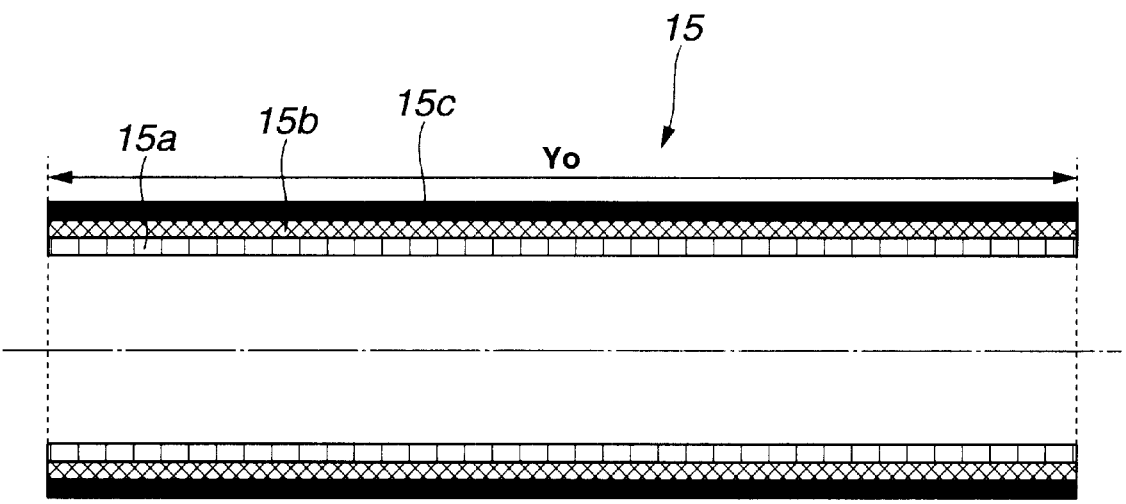
FIG. 3A and FIG. 3B are diagrams depicting a configuration and a function of the flexible tube.
Figure 3B:
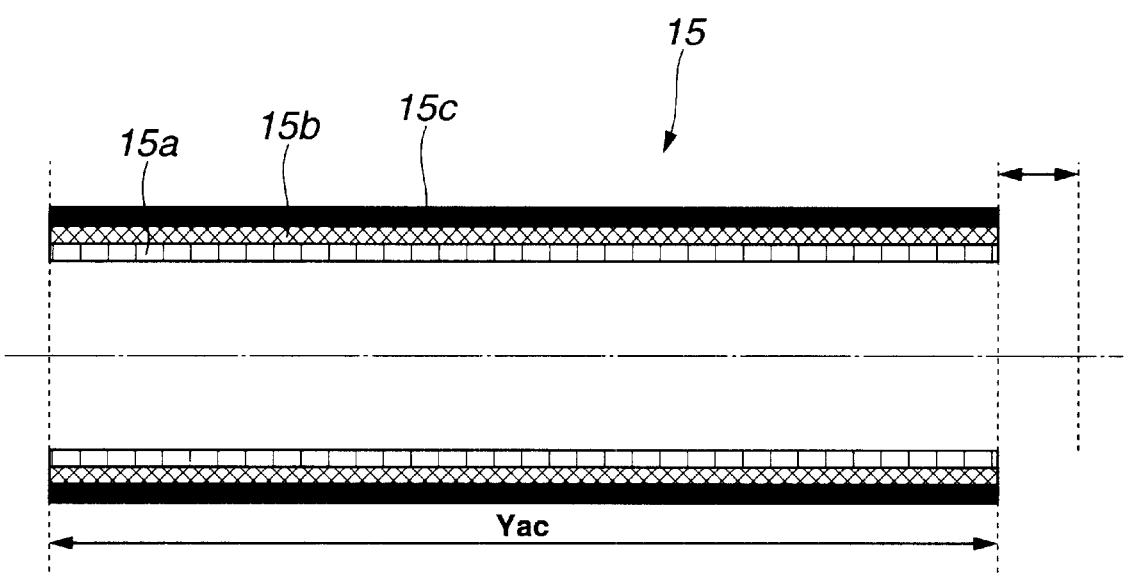

FIGS. 1 to FIG. 4 are related to an embodiment of the present invention, wherein FIG. 1 is a diagram depicting a general configuration of the endoscope device, FIG. 2 is a diagram depicting an example of a configuration of the insertion part, FIG. 3A and FIG. 3B are diagrams depicting a configuration and a function of the flexible tube, and FIG. 4 is a diagram depicting a configuration and a function of the elongated integrated object.

Figure 4A:
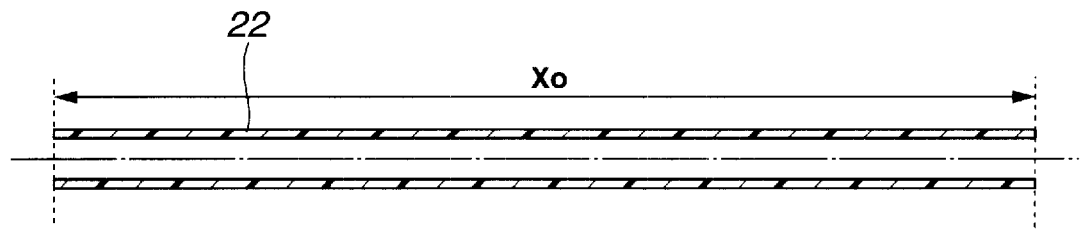
FIG. 4A and FIG. 4B are diagrams depicting a configuration and a function of the elongated integrated object.
Figure 4B:
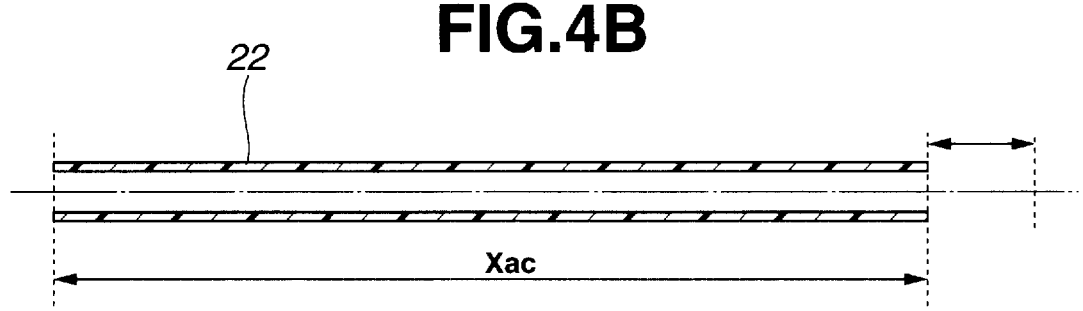

FIG. 3A is a diagram depicting the initial status of the flexible tube, FIG. 3B is a diagram depicting the flexible tube after a predetermined thermal load is applied, FIG. 4A is a diagram depicting the initial status of the integrated object, and FIG. 4B is a diagram depicting the integrated object after a predetermined thermal load is applied.

As FIG. 1 shows, the endoscope device 1 of the present invention comprises an electronic endoscope (hereinafter "endoscope") 2 having image pick-up means, a light source device 3 for supplying illumination light, a video processor 4 for controlling the image pick-up means and for processing the signals obtained from the image pick-up means, and a monitor 5 connected to this video processor 4. The numeral 50 indicates a later mentioned housing case for sterilization to house the endoscope 2.

The above mentioned endoscope 2 is comprised of an insertion part 10 which is elongated and is flexible, an operation part 11 which is linked to the end of the insertion part 10, and a universal cord 12 which extends from the side of the operation part 11 and is flexible. Located at the end of the universal cord 12, a connector 12a can be freely connected to/disconnected from the light source device 3. By connecting this connector 12a to the light source device 3, illumination light from the lamp (not shown), which is equipped to the light source device 3, is transmitted through the light guide (not shown) of the endoscope 2, and irradiates the observation part.

An insertion part bending prevention element 7a, which is comprised of an elastic element for preventing acute bending, is disposed at the connection part between the insertion part 10 and the operation part 11, a similar operation part bending protection element 7b is disposed at the connection part between the operation part 11 and the universal cord 12, and a similar connector bending protection element 7c is disposed at the connection part between the universal cord 12 and the connector 12a.

The insertion part 10, which is elongated and flexible, of the endoscope 2, is comprised of a hard tip part 13 which is hard and where an observation window and illumination window (not shown) are disposed at the tip face, a curving part 14 where a plurality of curving pieces are linked so as to be freely curved, and a flexible tube 15 which is flexible, which are all linked together. The curving part 14 curves by operating a curving control knob 16 disposed at the operation part 11, so that the tip face of the hard tip part 13 where an observation window etc. are disposed can be turned to a desired direction.

The operation part 11 comprises, in addition to the curving control knob 16, a gas supply/water supply operation button 17 for performing gas supply/water supply operation when cleaning liquid or gas is ejected from the gas supply/water supply nozzle (not shown) to the observation window, a suction operation button 18 for performing suction operation via a suction hole (not shown) on the tip face, a plurality of remote switches 19 for remote-controlling the video processor 4, and a treatment instrument insertion hole 20, which is linked to the treatment instrument channel disposed in the insertion part of the endoscope 2.

An electric connector part 12b is disposed on the side of the connector 12a. In this electric connector part 12b, the signal connector 6a of the signal cord 6 connected to the video processor 4 is attachably and detachably connected freely. By connecting this signal connector 6a to the video processor 4, the image pick-up means of the endoscope 2 is controlled, and image signals are generated by the electric signals transmitted from this image pick-up means so as to display the image observed by the endoscope on the screen of the monitor 5. A vent hole (not shown) linking the inside and outside of the endoscope 2, is formed on the electric connector part 12b. Therefore, a water-proof cap with a pressure regulating valve (hereinafter "water-proof cap") 9a, which has a pressure regulating valve (not shown) to block the vent hole, is freely attached and detached to/from the electric connector part 12b of the endoscope 2.

In the connector 12a, a gas supply mouth piece 12c which is attachably and detachably connected to the gas supply source (not shown) freely, and which is incorporated into the light source device 3, a water supply tank pressure mouth piece 12d and a liquid supply mouth piece 12e which are attachably and detachably connected to a water supply tank 8 freely, that is, the liquid supply source, a suction mouth piece 12f where a suction source (not shown) for sucking from the suction hole are connected, and an injection mouth piece 12g, which is connected to the water supply means (not shown) for supplying water, are disposed.

An earth terminal mouth piece 12h is disposed to feedback the leak current to the high frequency treatment device (not shown) when high frequency leak current is generated in the endoscope 2 at high frequency treatment.

The endoscope 2 is configured such that autoclaving after cleaning is possible when the endoscope is used for observation and treatment, and when the endoscope 2 is autoclaved, the water-proof cap 9a is attached to the electric connector part 12b.

And when the endoscope 2 is autoclaved, this endoscope 2 is housed in the housing case for sterilization 50. This housing case for sterilization 50 is comprised of a tray 51, which is the main unit, and the cover element 52, and in the tray 51, control elements (not shown) matching the shape of the endoscope, are arranged so that the insertion part 10, the operation part 11, the universal cord 12, the connector 12a and other components of the endoscope 2 are housed at predetermined positions. On the tray 51 and the cover element 52, a plurality of vent holes are formed to guide high pressure steam.

As FIG. 2 shows, the insertion part 10 is comprised of a hard tip part 13, a curving part 14, and a flexible tube 15, which is linked to the base of the hard tip part 13 via the curving part 14.

A metal pipe 21 is secured to the through hole 13a, which is formed at the hard tip part 13 and which functions both as, for example, a suction hole and treatment instrument channel. The tip of a tube for inserting treatment instrument (hereinafter treatment instrument tube) 22, which is at least an elongated integrated object, is secured to this metal pipe 21. This treatment instrument tube 22 is normally a resin tube made of PTFE (polytetrafluoroethylene) or the like. The treatment instrument tube 22 is inserted through the flexible tube 15, and the base part of the treatment instrument tube 22 is secured to the branch pipe 23.

A connecting pipe 24 is secured at the base of the flexible tube 15. A branch pipe 23 is secured to this connecting pipe 24 via a connecting element 25. A treatment instrument pipe line 20a, which links to the treatment instrument insertion hole 20, and a tube for section 26 which is guided from the operation part 11, are connected to the branch pipe 23.

In this embodiment, both ends of the flexible tube 15 and the treatment instrument tube 22 are indirectly secured, but the flexible tube 15 and the treatment instrument tube 22 may be directly secured by integrating the connecting pipe 24 and the branch pipe 23.

Also, in this embodiment, the treatment instrument tube 22 is shown as an elongated integrated object, but a tube for supplying gas or water, or tubes used for other purposes may be used, however these are not shown.

As FIG. 3A shows, the flexible tube 15 is comprised of a spiral tube 15a where a thin strip of metal is wound in a spiral shape, a meshed tube 15b where fine metal wires are woven, and a covering resin 15c, are layered in this sequence from the inner layer side. The covering resin 15c is made of, for example, such resin materials as ester thermoplastic elastomer, amide thermoplastic elastomer, styrene resin, fluoro rubber and silicon rubber. The above mentioned universal cord 12 also has a similar configuration as this flexible tube 15.

The flexible tube 15 has length Yo, as shown in FIG. 3A, in the initial status. When a predetermined thermal load is applied to the flexible tube 15, the length of the flexible tube 15 changes to Yac, as shown in Fib. 3B. The relationship between the dimensions Yo and Yac can be determined by experiment, and the shrinkage factor y of the flexible tube 15 in the length direction can be defined as follows.

$Y=Yac/Yo$

The treatment instrument tube 22, on the other hand, has length Xo, as shown in FIG. 4A, in the initial status. When a predetermined thermal load is applied to the treatment instrument tube 22, the length of the treatment instrument tube 22 changes to Xac, as shown in FIG. 4B. The relationship between the dimensions Xo and Xac can be determined by experiment, and the shrinkage factor x of the treatment instrument tube 22 in the length direction can be determined as follows.

$X=Xac/Xo$

When the flexible tube 15 having the characteristic y<1, that is, the flexible tube 15 which has a characteristic of shrinking after a predetermined thermal load is applied is used, for example, based on the shrinkage factors x and y defined as above in the present embodiment, the treatment instrument tube 22 having characteristic x<1, that is, the treatment instrument tube 22 which has a characteristic of shrinking after a predetermined thermal load is applied, is used in a configuration, in other words, the flexible tube and the treatment instrument tube are set to be deformed in some directions, as a deformation control means.

If the flexible tube 15 having a characteristic y>1, which elongates after a predetermined thermal load is applied, is used for the above mentioned flexible tube 15 of the endoscope 2, then the treatment instrument tube 22, having a characteristic x>1 and which elongates after a predetermined thermal load is applied, is used in the configuration.

The functions when the endoscope 2 configured as above is autoclaved will now be described.

At first the typical conditions of autoclave sterilization will be described.

Typical conditions are four minutes in the sterilization process at 132 C in the case of a pre-vacuum type, or 10 minutes in the sterilization process at 132 C in the case of a gravity type, according to the US standard ANSI/AAMI ST 37-1992, approved by the American National Standards Institute, as issued by the Association for the Advancement of Medical Instrumentation.

The temperature conditions during the sterilization process of autoclave sterilization differs depending on the type of autoclave sterilizer and the time of the sterilization process, but is normally set in a 115 C to 138 C range. Some sterilizers may be set to about 142 C.

Time conditions differ depending on the temperature conditions of the sterilization process. Normally time is set from 3 to 60 minutes. Some sterilizers may be set to about 100 minutes.

The pressure inside the sterilization chamber in this process is normally set to about +0.2 MPa with respect to the atmospheric pressure.

Now the autoclave sterilization process of a general pre-vacuum type endoscope will be described in brief.

At first, a water-proof cap 9a is attached to the electric connector part 12b of the endoscope 2 which is the autoclaving target, the endoscope is housed in the housing case for sterilization 50, and the housing case is disposed in the sterilization chamber. By the water-proof cap 9a attached to the electric connector part 12b, the pressure regulating value is closed which closes the vent hole. In other words, the inside of the endoscope 2 is sealed water-tight from the outside. Then the pressure inside the sterilization chamber before the autoclave sterilization process is reduced (pre-vacuum process).

The pre-vacuum process is for infiltrating steam into the sterilization target equipment during the sterilization process, and by reducing the pressure in the sterilization chamber, high pressure high temperature steam spreads through the entire sterilization target equipment. The pressure in the sterilization chamber in the pre-vacuum process is normally set to about −0.07 to −0.09 MPa with respect to the atmospheric pressure.

When pressure in the sterilization chamber decreases in the pre-vacuum process, a pressure difference is generated since the external pressure of the endoscope 2 becomes lower than the internal pressure. Then the pressure regulating valve of the water-proof cap 9a opens, and inside and outside the endoscope 2 are connected via the vent hole. This prevents the pressure difference from becoming too large. In other words, damage to the endoscope 2, due to the pressure difference between the internal pressure and the external pressure, is prevented.

Then high pressure high temperature steam is supplied to the sterilization chamber, and sterilization is executed (sterilization process).

The inside of the sterilization chamber is pressurized during this sterilization process. Then a pressure difference is generated, where the external pressure of the endoscope 2 is higher than the internal pressure. As a result, the pressure regulating valve of the water-proof cap 9a closes, so as to block high pressure steam from passing through the vent hole, entering into the endoscope.

However, high pressure steam gradually enters into the endoscope, passing through the covering resin 15c of the flexible tube 15, which is made of polymer material, or passing through the O ring, made of fluorine rubber or silicon rubber, which is a sealing means disposed at the connection part of the outer body of the endoscope 2.

At this time, pressure, which is the sum of the pressure reduced in the pre-vacuum process and the pressure pressurized in the sterilization process, is generated from the outside to the inside of the outer body of the endoscope 2.

Then to dry the sterilization target equipment after sterilization, a drying (dry process) is executed by setting the inside of the stabilization chamber into a pressure reduced status again after the sterilization process ends. In this dry process, drying the sterilization target equipment in the sterilization chamber is promoted by reducing the pressure inside the sterilization chamber in order to release steam from the sterilization chamber. The pressure in the sterilization chamber in the dry process is normally set to about −0.07 MPa −0.09 MPa with respect to the atmospheric pressure. The above mentioned dry process is executed arbitrarily if required.

In the pressure reduction process after the sterilization process, pressure inside the sterilization chamber decreases, and a pressure difference is generated where the external pressure of the endoscope 2 is lower than the internal pressure. When this pressure difference is generated, the pressure regulating valve of the water-proof cap 9a opens roughly at the same time, and the inside and the outside of the endoscope 2 are connected via the vent hole, so as to prevent generating a large pressure difference between the inside and the outside of the endoscope. When the pressure reduction process ends, and the inside of the sterilization chamber is pressurized and returns to the atmospheric pressure, the pressure regulating valve of the water-proof cap 9a closes as a pressure difference is generated, where the external pressure of the endoscope 2 is higher than the internal pressure.

When all the processes of autoclave sterilization completes, pressure for the amount reduced in the dry process is generated from the outside to the inside of the outer body of the endoscope 2. By removing the water-proof cap 9a from the electric connector part 12b, the inside and the outside of the endoscope 2 is connected via the vent hole, the inside of the endoscope 2 becomes the atmospheric pressure, and the load due to the pressure difference generated onto the outer body of the endoscope 2 disappears.

As described above, in the sterilization process, both the flexible tube 15, having a characteristic y<1, constituting the endoscope 2, and the treatment instrument tube 22, having a characteristic x<1, are exposed to high pressure steam. Since a predetermined thermal load is applied to the flexible tube 15 and the treatment instrument tube 22, both tubes shrink in longitudinal directions.

When the shrinkage factor y and the shrinkage factor x have the relationship y≠x, a difference is generated between the deformation amount of the flexible tube 15, having a characteristic y<1, in the longitudinal direction, and the deformation amount of the elongated treatment instrument tube 22, having a characteristic x<1, in the longitudinal direction.

Here, when the absolute value of the difference between the deformation amount of the flexible tube 15 in the longitudinal direction and the deformation amount of the treatment instrument tube 22 in the longitudinal direction in the combination of the flexible tube 15, having a characteristic y<1, and the treatment instrument tube 22, having a characteristic x<1, is compared with the absolute value of the difference between the deformation amount of the flexible tube 15 in the longitudinal direction and the deformation amount of the treatment instrument tube 22 in the longitudinal direction in the combination of a flexible tube 15, having a characteristic y≈1 and a treatment instrument tube 22, having a characteristic x>1, or a combination of a flexible tube 15, having a characteristic y≈1 and a treatment instrument tube 22, having a characteristic x<1, or a combination of a flexible tube 15, having a characteristic y>1 and a treatment instrument tube 22, having a characteristic x≈1, or a combination of a flexible tube 15, having a characteristic y>1 and a treatment instrument tube 22, having a characteristic x<1, or a combination of a flexible tube 15, having a characteristic of y<1 and a treatment instrument tube 22, having a characteristic x≈1, or a combination of a flexible tube 15, having a characteristic y<1 and a treatment instrument tube 22, having a characteristic x>1, the deformation amount is controlled most with the combination of the above mentioned flexible tube 15 and the treatment instrument tube 22 of the present embodiment, since the deforming direction (shrinking direction in the case of the present embodiment) is the same.

By setting the deformation direction of the flexible tube and the elongated integrated object in the same direction with respect to the longitudinal direction in this way, a major change of the deformation amount in the longitudinal direction can be prevented when the endoscope is exposed to such a thermal load environment as autoclave sterilization, because if the flexible tube is deformed in the shrinking direction, the integrated object is also deformed in the shrinking direction.

As a result, a relative loosening of the elongated integrated object with respect to the flexible tube and the pressing of other integrated objects, or applying a load on the fixed parts at both ends of the integrated object by a relative stretching of the elongated integrated object with respect to the flexible tube and damaging the fixed parts, or curving operation problems, such as when curving does not occur in a desired direction when the curving operation is executed, can be prevented.

In the shrinkage factors x and y defined in this embodiment, if the flexible tube 15 and the treatment instrument tube 22, having characteristics x<y≈1, are combined, annealing processing is performed before assembling the treatment instrument tube 22.

Here a condition of the annealing processing is a temperature where the treatment instrument tube 22 does not deform in the longitudinal direction after autoclave sterilization, that is, a temperature where the treatment instrument tube 22 has completely shrunk. Therefore, the temperature of annealing need not be the same as the temperature load to be applied during autoclave sterilization, but may be less, however it is preferable to set this temperature to be roughly the same as the temperature load to be applied during autoclave sterilization, that is, 115 C.–138 C., however the temperature may be set to a temperature higher than 138 C. since a setting of 142 C. may be acceptable depending on the autoclave sterilizer.

By performing annealing processing on the treatment instrument tube 22 before assembly in this way, the shrinkage factor x' of the treatment instrument tube 22 after annealing becomes x≈1, that is, x'≈y, since the above mentioned shrinkage factor y is y≈1, therefore a major difference is not generated in the deformation amount at both elements when a predetermined thermal load is applied. In other words, functions and effects similar to the above mentioned embodiment can be obtained. If x>y≈1, similar functions and effects are obtained by performing the annealing processing on the treatment instrument tube 22 in the same manner in advance.

With the shrinkage factors x and y defined in the above mentioned embodiment, if a flexible tube 15 and a treatment instrument tube 22 having characteristics y<x≈1 are combined, annealing processing is executed before assembling the flexible tube 15. By performing annealing processing on the flexible tube 15 before assembly, the shrinkage factor y' of this flexible tube 15 after annealing becomes y'≈1, that is, y'≈x, since the above mentioned shrinkage factor x is x≈1, therefore a major difference of the deformation amount of both elements is not generated when a predetermined thermal load is applied. In other words, functions and effects similar to the above mentioned embodiment can be obtained. If y>x≈1, similar functions and effects are obtained by performing annealing processing on the flexible tube 15 in the same manner in advance.

With the shrinkage factors x and y defined in the above mentioned embodiment, if a flexible tube 15 and a treatment instrument tube 22, having characteristics x<y or x>y, are combined, annealing processing is performed on both the flexible tube 15 and the treatment instrument tube 22 before assembly. By this, the shrinkage factor x' of the treatment instrument tube 22 after annealing becomes x'≈1, and the shrinkage factor y' of the flexible tube 15 after annealing becomes y'≈1, that is, x'≈y'≈1, therefore a major difference is not generated in the deformation amount of both elements when a predetermined thermal load is applied. In other words, functions and effects similar to the above mentioned embodiment can be obtained.

With the shrinkage factors x and y defined in the above mentioned embodiment, if a flexible tube 15 and a treatment instrument tube 22, having characteristics x≈y, are combined, the length of the flexible tube 15 and the treatment instrument tube 22 are set to roughly the same. By this, a major difference is not generated in the deformation amount of both elements when a predetermined thermal load is applied, since the shrinkage factor of the flexible tube 15 and the treatment instrument tube 22 are almost the same. In other words, functions and effects similar to the above mentioned embodiment can be obtained. If the length of the flexible tube 15 and the treatment instrument tube 22 are extremely different, the deformation amount of the longitudinal direction, and not the shrinkage factor, are set to roughly the same.

An autoclave sterilizer was used as a means of applying the above mentioned predetermined thermal load, but if an autoclave sterilizer is used as a means of annealing processing, it is unnecessary to prepare a dedicated device for annealing.

When a tube element, such as the treatment instrument tube 22, which is an elongated integrated object, is annealed, it is desirable that the tube element not be curled.

Figure 5:
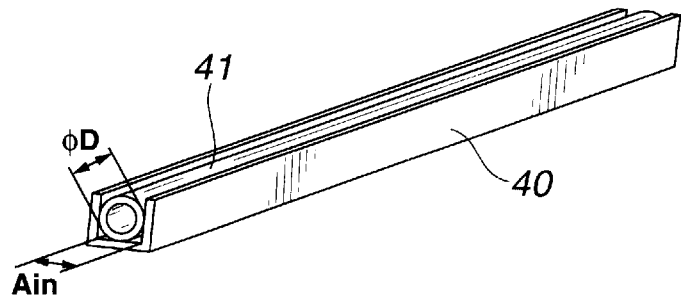
FIG. 5 is a diagram depicting an example of a configuration of the curling prevention element.

As FIG. 5 depicting a configuration example of the curling prevention element shows, according to the present embodiment, this tube element 41 is disposed in the curling prevention element 40, where the cross-section has a squared "U" shape when annealing processing is performed on the tube element 41 which is an elongated integrated objects.

The length of the curling prevention element 40 is roughly the same as the tube element 41, and the inner width Ain of the curling prevention element 40 is set to a dimension slightly larger than the outer diameter φD of the tube element 41. That is, the relationship is Ain>φD.

By disposing the tube element 41 in the curling prevention element 40 and performing annealing processing, the external side of the tube is controlled during annealing, and the tube element 41 is maintained in a straight status, so the tube element 41 is not curled after annealing.

In this way, the curling of an integrated object after annealing processing can be prevented by disposing the elongated integrated object in the curling prevention element when the elongated integrated object is annealed. As a result, the annealed integrated object is prevented from pressing other integrated objects, and the insertion of the endoscope is not affected.

Figure 6:
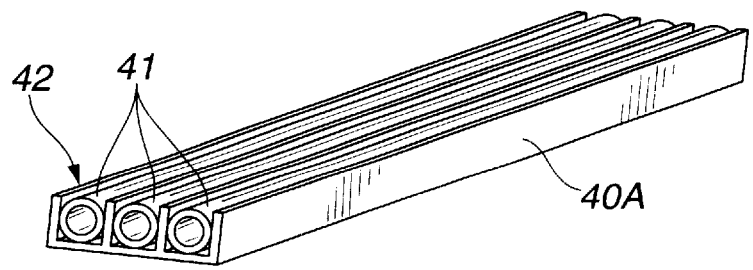
FIG. 6 is a diagram depicting another example of a configuration of the curling prevention element.

As FIG. 6 depicting another configuration example of the curling prevention element shows, a plurality of tube elements 41 can be annealed at the same time by configuring the curling prevention element 40A with a plurality of slots 42 having a squared U-shaped cross-section. Thereby, the efficiency of annealing processing of a tube element dramatically improves. In FIG. 6, there are three slots 42, but the number of the slots 42 may be more or less.

Figure 7:
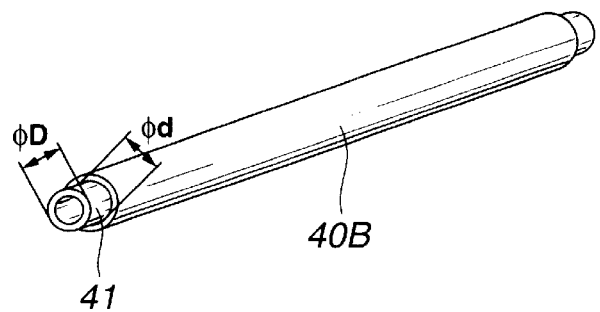
FIG. 7 is a diagram depicting another example of a configuration of the curling prevention element.

Instead of using the curling prevention element 40 with squared U-shaped cross-section, the tube element 41 may be disposed in an elongated pipe type curling prevention element 40B, as shown in FIG. 7, which depicts another configuration example of the curling prevention element. The length of this curling prevention element 40B may be roughly the same as the length of the tube element 41, but it is preferable that the length of the curling prevention element 40B is set to a dimension slightly shorter than the length of the tube element 41, considering the case of handling when the tube element 41 is removed after annealing processing.

It is preferable that the inner diameter φd of the curling prevention element 40B is set to a dimension slightly larger than the outer diameter φD of the tube element 41 (φd>φD). The setting may be about φd≈2φD considering that the outer diameter φD of the tube element 41 increases after annealing processing.

As a result, functions and effects similar to the curling prevention element 40 can be obtained. Also by setting the relationship between the inner diameter φd of the curling prevention element 40B and the outer diameter φD of the tube element 41 to be about φd≈2φD, the tube element 41 can be easily removed from the curling prevention element 40B, even if the outer diameter φD of the tube element 41 increases after annealing.

Figure 8:
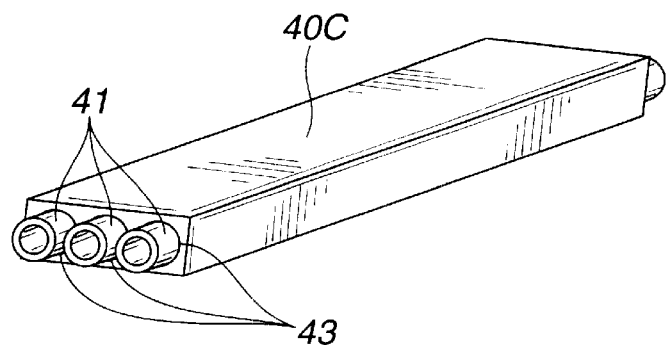
FIG. 8 is a diagram depicting another example of a configuration of the curling prevention element.

As FIG. 8 depicting another configuration example of the curling prevention element shows, a plurality of tube elements 41 can be annealed all at once by configuring the curling prevention element 40C by forming a plurality of through holes 43 with φd. In FIG. 8, there are three through holes 43, but the number of through holes 43 may be more or less.

When the above mentioned curling prevention element 40, 40A, 40B or 40C is configured, it need not have an integrated configuration, but the configuration may be separated into two or more parts.

Figure 9:
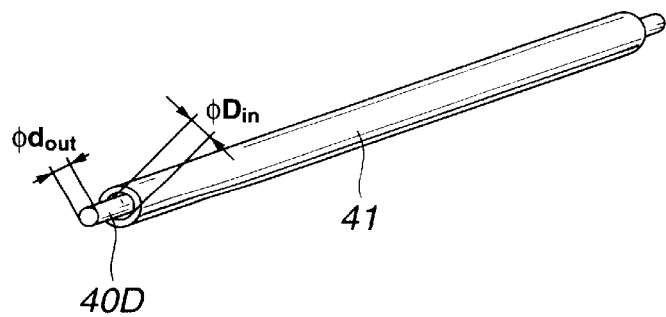
FIG. 9 is a diagram depicting another example of a configuration of the curling prevention element.

As FIG. 9 depicting another configuration example of the curling prevention element shows, the elongated core bar, which can be disposed inside the through hole of the tube element 41, may be used as the curling prevention element 40D. In this case, the length of the curling prevention element 40D, which is inserted into the inner hole of the tube element 41, may be roughly the same as the tube element 41, but it is preferable that the length of the curling prevention element 40D is set to a dimension slightly longer than the length of the tube element 41, considering the case of handling when the tube element 41 is removed after annealing processing.

It is preferable that the outer diameter φdOUT of the curling prevention element 40D is set to a diameter slightly smaller than the inner diameter φDIN of the tube element 41. The setting may be φdOUT≈0.5φDIN (that is, 2φdOUT≈φDIN) considering that the inner diameter φDIN of the tube element 41 decreases after annealing.

As a result, functions and effects similar to the curling prevention elements 40 and 40B can be obtained. Also, by setting the relationship between the outer diameter φdOUT of the curling prevention element 40D and the inner diameter φDIN of the tube element 41 to be about φdOUT≈0.5φDIN (that is, 2φdOUT≈φDIN), the tube element 41 can be easily removed from the curling prevention element 40D, even if the inner diameter φDIN of the tube element 41 decreases after annealing processing.

Now, how to set the length of the tube element 41 and the flexible tube 15 will be described.

As FIG. 2 shows, the dimensions of the tube element 41 and the flexible tube 15 at manufacturing, that is, the length thereof before annealing, are set considering the difference between the shrinkage amount of the flexible tube 15 and the shrinkage amount of the tube element 41 at annealing, so as to remove the loosening of the tube element 41. For example, the length of the integrated object is set to be longer for the shrinkage amount of the flexible tube.

Figure 10:
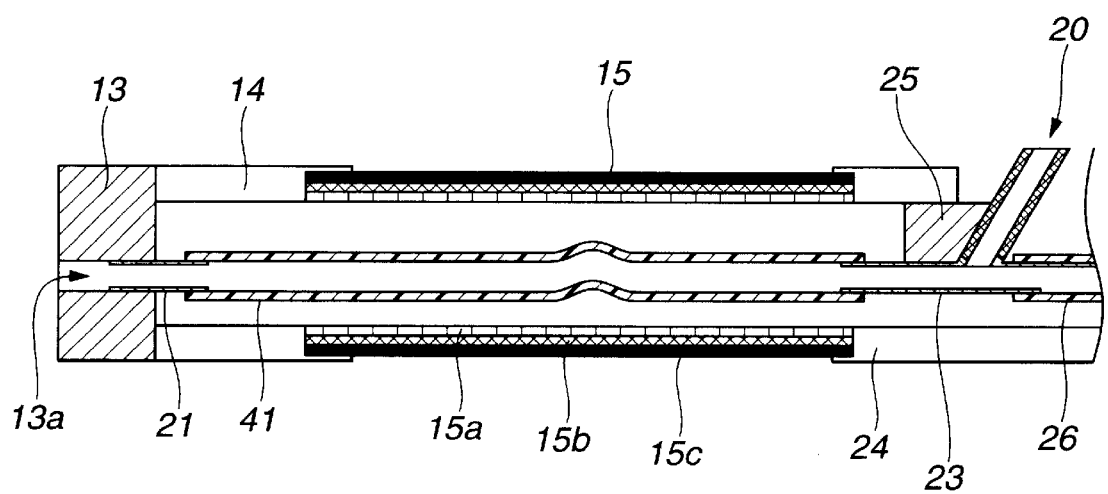
FIG. 10 is a diagram depicting a relationship between the flexible tube and tube element during manufacturing.

So when the endoscope 2 is configured incorporating the tube element 41 into the flexible tube 15 during manufacturing, some degree of loosening is generated to the tube element 41, as shown in FIG. 10 depicting the relationship between the flexible tube and the tube element during manufacturing.

In other words, according to this embodiment, the length Ys of the flexible tube 15 during manufacturing before annealing, and the length Xs of the tube element 41 during manufacturing before annealing are designed to satisfy the following formula so that loosening is removed, as shown in FIG. 2, when the tube element 41 is incorporated into the flexible tube 15 and is annealed in this state.

$$Ys(1-y)=Xs(1-x)$$

Here x and y are the above mentioned shrinkage factors. If the flexible tube 15 and the tube element 41 are indirectly connected, an appropriate constant is added, and the lengths Ys' and Xs' are designed so as to satisfy the following formula.

$$Ys'(1-y)=Xs'(1-x)$$

$$Xs'=Xs+P$$

$$Ys'=Ys+Q$$

Here the constants P and Q are determined by the dimension of the connecting element when the connection is indirect, and if the flexible tube 15 and the tube element 41 are connected as shown in FIG. 10, for example, these constants P and Q are determined by the dimensions of the curving part 14, the hard tip part 13, and the metal pipe 21 in the longitudinal direction, and the dimensions of the connecting pipe 24, the connecting element 25 and the branch pipe 23 in the longitudinal direction.

By designing the lengths of the flexible tube and the tube element during manufacturing considering the dimensional change in the annealing processing in this way, a major change of the deformation amount in the flexible tube and the tube element in the longitudinal direction can be prevented when a thermal load, such as in autoclave sterilization, is applied to the endoscope.

The length of the tube element after annealing may be set such that the tube element slightly loosens with respect to the flexible tube, so as not to press other integrated objects. For example, the length of the integrated object is set to be roughly longer for the same amount of shrinkage of the integrated object with respect to the flexible tube.

By annealing in the state, as shown in FIG. 10, where the tube element 41 is incorporated into the flexible tube 15 during manufacturing to constitute the endoscope 2, the endoscope 2 has a configuration where the tube element 41 is disposed without loosening, as shown in FIG. 2.

As a result, a major change of the deformation amount of the flexible tube and the tube element in the longitudinal direction after autoclave sterilization is prevented, and also if a plurality of integrated objects are in the insertion part not only have elongated integrated objects but also other resin-molded parts can be annealed all at once after assembly, since annealing processing is performed after assembling the endoscope. Also, the flexible tube and the tube element are not curled during annealing, even if the curving prevention element is not used, and the above mentioned problem caused by stretching the integrated object does not occur.

By annealing after assembling the endoscope, a shipment inspection can be performed in the status and performance after autoclave sterilization.

A condition of annealing can be a temperature condition which is about the same as or higher than the temperature load of autoclave sterilization.

When a material which has a characteristic whereby length changes during the autoclave sterilization process is used, this change amount must be considered when length is set, even if the above mentioned annealing is executed,.

If the length during manufacturing, which was set, is in a range which does not negatively affect other integrated objects in the flexible tube, the endoscope is shipped without annealing during manufacturing. When an autoclave sterilizer is used, the relationship between the tube element and the flexible tube reaches an appropriate length. Critical here is that the length during manufacturing is set such that no problems occur due to the length change of the flexible tube and the integrated object by such a thermal load as an autoclave sterilization process.

Having described the preferred embodiments of the invention referring to the accompanying drawings, it is to be understood that the invention is not limited to those precise embodiments and that various changes and modifications thereof could be effected by one skilled in the art without departing from the spirit or scope of the invention as defined in the appended claims.

What is claimed is:

1. A method of controlling a relative deformation of an endoscope, the method comprising:
providing an endoscope having a flexible insertion part having an elongated flexible tube and at least one elongated integrated object which is directly or indirectly secured to both ends of said flexible tube; and
controlling shrinkage factors of said flexible tube and said integrated object to prevent a substantial relative deformation of the flexible tube with respect to the integrated object upon heat sterilization of the endoscope.

2. The method according to claim 1, said controlling comprises applying a predetermined thermal load to at least one of said flexible tube and said integrated object before assembly of said flexible tube so that shrinkage factors of said flexible tube and said integrated object become roughly the same.

3. The method of claim 2, said applying comprises annealing processing.

4. The method of claim 3, said annealing comprises applying temperature conditions roughly the same or higher than temperature load conditions during an autoclave sterilization process.

5. The method of claim 3, said annealing comprises using a curling prevention element for keeping the integrated object in a straight status.

6. The method of claim 5, said using enclosing said integrated object inside said curling prevention element.

7. The method of claim 5, said using inserting the curling prevention element into an inner hole of said integrated object.

8. The method of claim 2, said applying comprises an autoclave sterilization process.

9. The method according to claim 1, said controlling comprises setting a deformation direction of said integrated object and a deformation direction of said flexible tube with respect to a thermal load to a same direction.

10. The method of claim 1, said controlling comprises setting a deformation amount in the longitudinal direction of said flexible tube and said integrated object with respect to said predetermined thermal load to be roughly the same.

11. The method of claim 1, said controlling comprises setting a length of the integrated object to be incorporated into said flexible tube to a dimension longer than a shrinkage amount of the flexible tube when a predetermined thermal load is applied.

12. The method of claim 1, said controlling comprises performing annealing of said integrated object in an endoscope manufacturing process after incorporating said integrated object in the flexible tube.

13. The method of claim 1, said controlling comprises setting a length of said integrated object to a dimension longer than a shrinkage amount of said integrated object with respect to said flexible tube.

* * * * *